(12) United States Patent
Nuno et al.

(10) Patent No.: US 12,264,834 B2
(45) Date of Patent: Apr. 1, 2025

(54) AIR CONDITIONER

(71) Applicant: DAIKIN INDUSTRIES, LTD., Osaka (JP)

(72) Inventors: Hayato Nuno, Osaka (JP); Hiroshi Itou, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 307 days.

(21) Appl. No.: 17/706,014

(22) Filed: Mar. 28, 2022

(65) Prior Publication Data

US 2022/0214069 A1    Jul. 7, 2022

Related U.S. Application Data

(63) Continuation of application No. PCT/JP2020/034321, filed on Sep. 10, 2020.

(30) Foreign Application Priority Data

Sep. 30, 2019  (JP) .................................. 2019-180008

(51) Int. Cl.
*F24F 11/64*    (2018.01)
*A61L 2/10*    (2006.01)
(Continued)

(52) U.S. Cl.
CPC .................. *F24F 11/64* (2018.01); *A61L 2/10* (2013.01); *C02F 1/325* (2013.01); *F24F 13/22* (2013.01); *A61L 2202/11* (2013.01); *A61L 2202/14* (2013.01); *C02F 2201/326* (2013.01); *C02F 2209/02* (2013.01); *C02F 2209/42* (2013.01);
(Continued)

(58) Field of Classification Search
CPC ...... F24F 11/64; F24F 13/22; F24F 2013/228; A61L 2/10; C02F 1/325; C02F 2201/326; C02F 2303/04; C20F 2209/02; C20F 2209/44
See application file for complete search history.

(56) References Cited

U.S. PATENT DOCUMENTS

2015/0328961 A1* 11/2015 Kim ..................... B60H 1/3202
                                                        62/190

FOREIGN PATENT DOCUMENTS

| CN | 108645002 A | 10/2018 |
| JP | 1-153419 U | 10/1989 |

(Continued)

OTHER PUBLICATIONS

Adachi (JP 2017133700 A), English Translation, 2017, Whole Document (Year: 2017).*

(Continued)

*Primary Examiner* — Larry L Furdge
*Assistant Examiner* — Keith Stanley Myers
(74) *Attorney, Agent, or Firm* — Birch, Stewart, Kolasch & Birch, LLP

(57) ABSTRACT

An air conditioner includes a heat exchanger provided in an indoor unit, a drain pan that receives drain water generated in the heat exchanger, an irradiation unit that irradiates the drain pan with ultraviolet rays, and a control unit that controls ultraviolet intensity of the irradiation unit. The control unit controls the irradiation unit to make the ultraviolet intensity after a cooling operation is larger than the ultraviolet intensity during the cooling operation.

15 Claims, 5 Drawing Sheets

(51) Int. Cl.
  *C02F 1/32* (2023.01)
  *F24F 13/22* (2006.01)
  *F24F 110/10* (2018.01)
  *F24F 110/12* (2018.01)
  *F24F 140/20* (2018.01)
  *F24F 140/30* (2018.01)

(52) U.S. Cl.
  CPC ...... *C02F 2209/44* (2013.01); *C02F 2303/04* (2013.01); *F24F 2013/228* (2013.01); *F24F 2110/10* (2018.01); *F24F 2110/12* (2018.01); *F24F 2140/20* (2018.01); *F24F 2140/30* (2018.01)

(56) References Cited

FOREIGN PATENT DOCUMENTS

| JP | 2000-111076 A | 4/2000 |
|---|---|---|
| JP | 2001-324195 A | 11/2001 |
| JP | 2005-95400 A | 4/2005 |
| JP | 2016-200290 A | 12/2016 |
| JP | 2017109535 A * | 6/2017 |
| JP | 2017-133700 A | 8/2017 |
| JP | 2018-189254 A | 11/2018 |
| JP | 2019-120431 A | 7/2019 |

OTHER PUBLICATIONS

Hama et al. (JP 2017109535 A), English Translation, 2017, Whole Document (Year: 2017).*

International Search Report, issued in PCT/JP2020/034321, PCT/ISA/210, dated Oct. 27, 2020.

Written Opinion of the International Searching Authority for PCT/JP2020/034321 mailed on Oct. 27, 2020.

International Preliminary Report on Patentability and English translation of the Written Opinion of the International Searching Authority for International Application No. PCT/JP2020/034321, dated Apr. 14, 2022.

Extended European Search Report for European Application No. 20872653.9, dated Sep. 16, 2022.

* cited by examiner

AIR CONDITIONER

CROSS REFERENCE TO RELATED APPLICATIONS

This application is a Continuation of PCT International Application No. PCT/JP2020/034321 filed on Sep. 10, 2020, which claims priority under 35 U.S.C. § 119 (a) to Patent Application No. 2019-180008 filed in Japan on Sep. 30, 2019, all of which are hereby expressly incorporated by reference into the present application.

TECHNICAL FIELD

The present disclosure relates to air conditioners.

BACKGROUND ART

There is known an air conditioner in which a drain pan where drain water is stored is irradiated with deep ultraviolet rays having a relatively short wavelength among the ultraviolet rays (see, for example, Japanese Laid-Open Patent Publication No. 2017-133700). The irradiation with deep ultraviolet rays causes denaturation or inactivation of bacteria, mold, or the like contained in the drain water (hereinafter, referred to as "sterilization").

SUMMARY

As disclosed in Patent Literature 1, when it is determined that the air conditioner is in cooling operation, irradiation with deep ultraviolet rays is started. Accordingly, the irradiation with deep ultraviolet rays continues without stop during the cooling operation. This causes the irradiation with deep ultraviolet rays to be made for a long time, which shortens the life of an irradiation unit responsible for the irradiation with deep ultraviolet rays.

The present disclosure provides an air conditioner that makes the life of an irradiation unit longer.

An air conditioner according to an aspect of the present disclosure includes: a heat exchanger provided in an indoor unit of the air conditioner, a drain pan configured to receive drain water generated in the heat exchanger, an irradiation unit configured to irradiate the drain pan with ultraviolet rays, and a control unit configured to control ultraviolet intensity of the ultraviolet rays from the irradiation unit. The control unit controls the irradiation unit to make the ultraviolet intensity after a cooling operation larger than the ultraviolet intensity during the cooling operation.

DESCRIPTION OF EMBODIMENT

Figure 1:
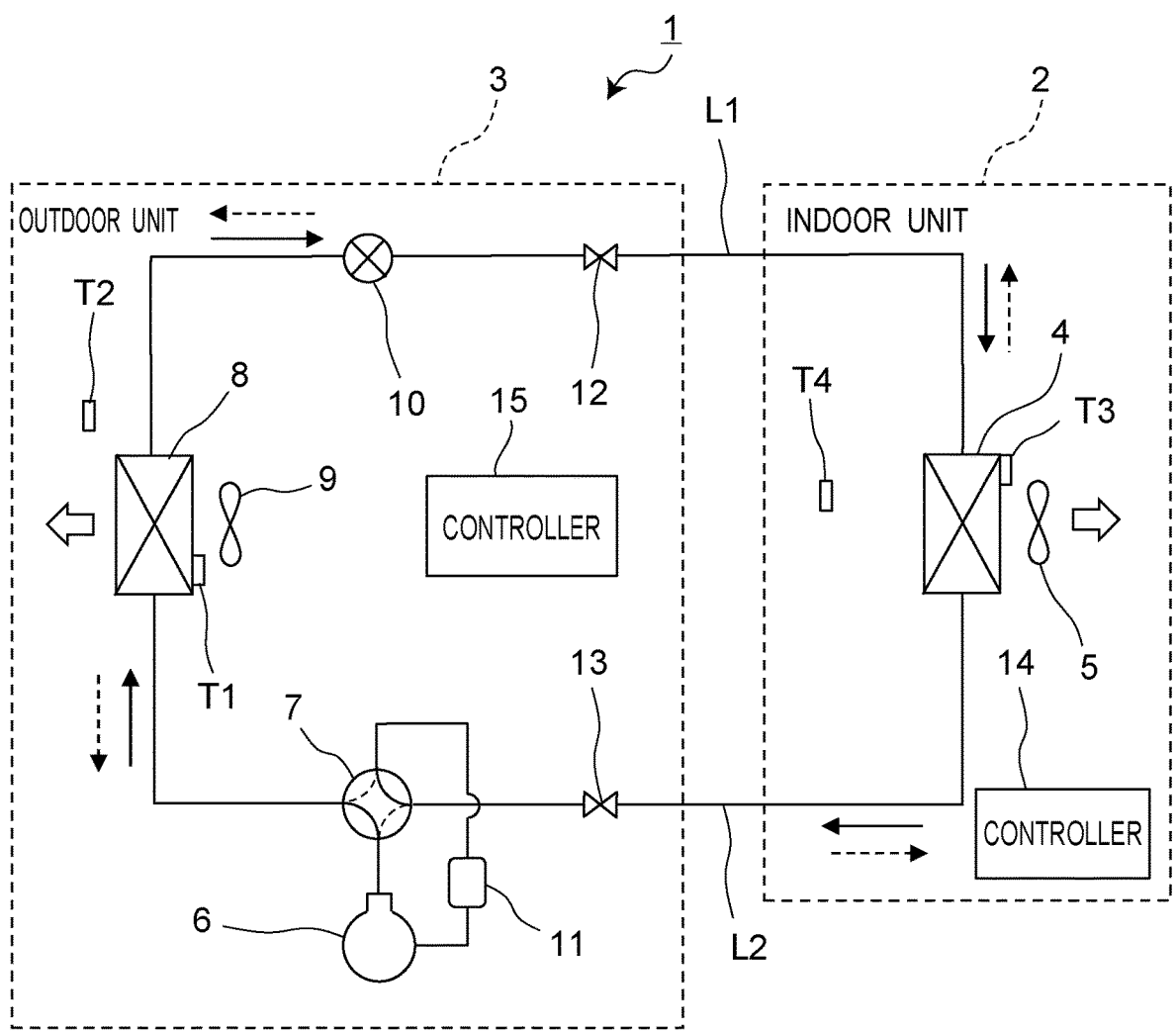
FIG. 1 is a diagram illustrating a refrigerant circuit of an air conditioner according to an embodiment.

Hereinafter, an air conditioner according to an embodiment of the present disclosure will be described with reference to the drawings. Note that the same parts in the drawings are denoted by the same reference sign, and no redundant description will be given.

[Overall Configuration of Air Conditioner 1]

FIG. 1 is a diagram illustrating a refrigerant circuit of an air conditioner 1 according to the embodiment of the present disclosure. As illustrated in FIG. 1, the air conditioner 1 includes an indoor unit 2 installed indoors and an outdoor unit 3 installed outdoors, the indoor unit 2 and the outdoor unit 3 being connected with each other via connection pipes L1, L2. The air conditioner 1 is of a type in which the indoor unit 2 is paired one-to-one with the outdoor unit 3.

The indoor unit 2 is equipped with an indoor heat exchanger 4 and an indoor fan 5. The outdoor unit 3 is equipped with a compressor 6, a four-way switching valve 7, an outdoor heat exchanger 8, an outdoor fan 9, an electric expansion valve (hereinafter, referred to as an expansion valve) 10 as an example of the decompressing mechanism, and an accumulator 11. The outdoor unit 3 is further provided with a liquid-side shutoff valve 12 and a gas-side shutoff valve 13.

The compressor 6, the four-way switching valve 7, the outdoor heat exchanger 8, the expansion valve 10, the indoor heat exchanger 4, the accumulator 11, and the compressor 6 are connected in this order via a refrigerant pipe and the connection pipes L1, L2 to form a refrigerant circuit. The liquid-side shutoff valve 12 is interposed between the expansion valve 10 and the connection pipe L1, and the gas-side shutoff valve 13 is interposed between the four-way switching valve 7 and the connection pipe L2.

In the refrigerant circuit, the compressor 6 has a discharge port connected to the outdoor heat exchanger 8 via the four-way switching valve 7 and has an intake port connected to the indoor heat exchanger 4 via the four-way switching valve 7 and the accumulator 11.

A remote controller 17 (hereinafter, referred to as a "remote control 17") can bring the air conditioner 1 configured as described above into cooling operation, dehumidifying operation, and heating operation. The remote control 17 can further switch or stop the operations, set an indoor temperature, set a rotational speed of the indoor fan 5, and the like.

During the cooling operation and the predetermined dehumidifying operation, a cooling cycle is established as indicated by solid arrows in which a refrigerant discharged from the compressor 6 sequentially flows from the four-way switching valve 7 to the indoor heat exchanger 4 through the outdoor heat exchanger 8 and the expansion valve 10 and returns to the compressor 6 through the four-way switching valve 7 and the accumulator 11. That is, the outdoor heat exchanger 8 functions as a condenser, and the indoor heat exchanger 4 functions as an evaporator. Note that, during the predetermined dehumidifying operation, although the indoor fan 5 is driven to an extent less than during the cooling operation, the refrigerant passing through the indoor heat exchanger 4 evaporates as a result of exchanging heat with indoor air. This causes moisture in the air to be condensed and collected on a surface of the indoor heat exchanger 4, thereby dehumidifying the air inside the room. Therefore, an operation during which condensed water is generated on the surface of the indoor heat exchanger 4 such as the cooling operation and the predetermined dehumidifying operation is herein referred to as a cooling operation.

On the other hand, during the heating operation, a heating cycle is established as indicated by dashed arrows in which the four-way switching valve 7 is switched to cause the refrigerant discharged from the compressor 6 to sequentially flow from the four-way switching valve 7 to the outdoor heat exchanger 8 through the indoor heat exchanger 4 and the expansion valve 10 and return to the compressor 6 through the four-way switching valve 7 and the accumulator 11. That is, the indoor heat exchanger 4 functions as a condenser, and the outdoor heat exchanger 8 functions as an evaporator.

As illustrated in FIG. 1, the indoor unit 2 is equipped with an indoor-unit controller (control unit) 14 that controls various operations of the indoor unit 2, and the outdoor unit 3 is equipped with an outdoor-unit controller (control unit) 15 that controls various operations of the outdoor unit 3. The air conditioner 1 is controlled as a whole by the indoor-unit controller (control unit) 14 or the outdoor-unit controller (control unit) 15, or under cooperation between the indoor-unit controller (control unit) 14 and the outdoor-unit controller (control unit) 15. Therefore, at least either the indoor-unit controller 14 or the outdoor-unit controller 15 acts as a control unit 16 that controls various operations of the air conditioner 1.

Figure 2:
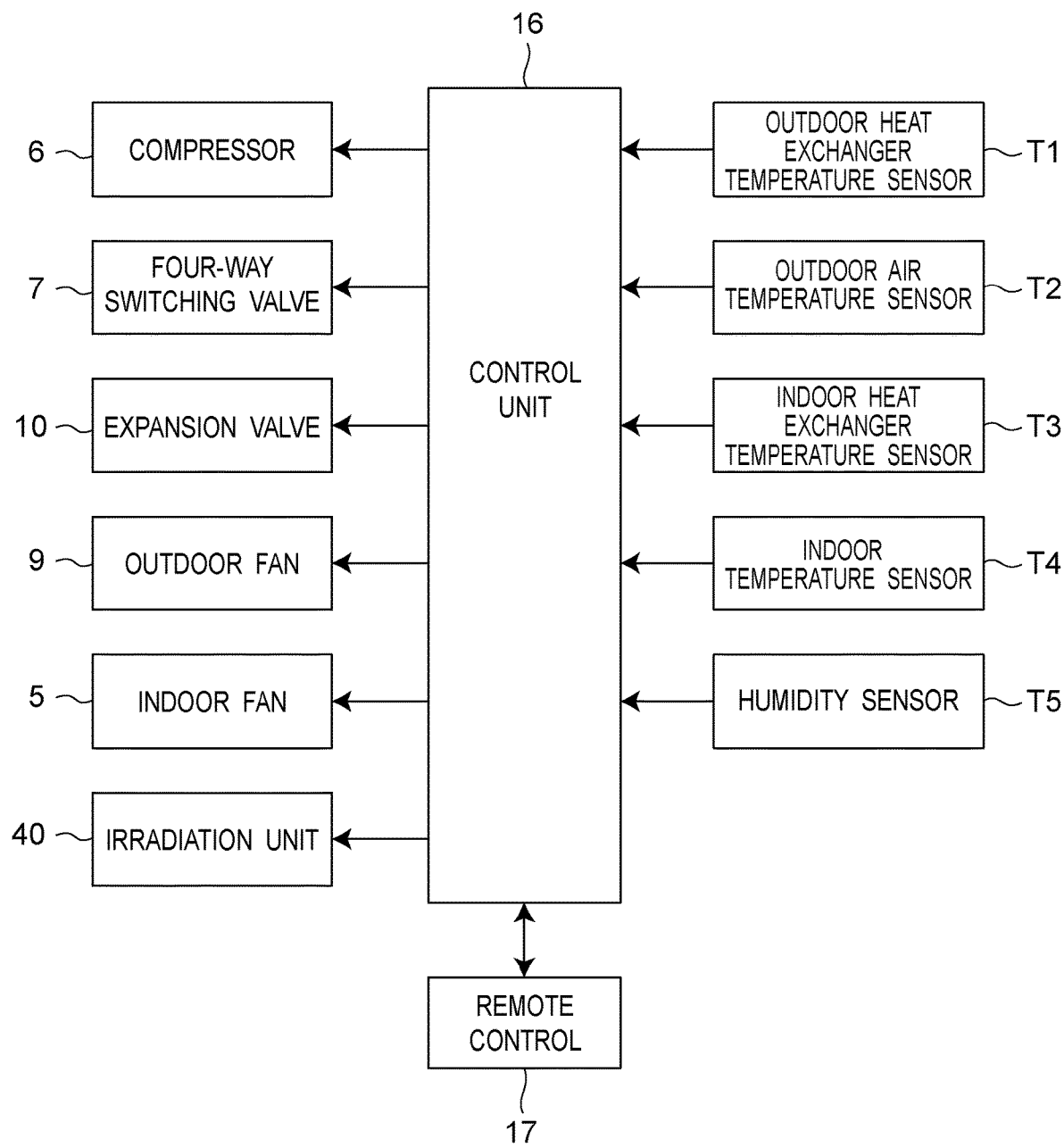
FIG. 2 is a control block diagram of the air conditioner illustrated in FIG. 1.

As illustrated in FIG. 2, the compressor 6, the four-way switching valve 7, the expansion valve 10, the indoor fan 5, and the outdoor fan 9 are connected to the control unit 16. Specifically, various drive units (e.g., a motor and a solenoid) for driving such components are connected to the control unit 16. An outdoor heat exchanger temperature sensor T1, an outdoor air temperature sensor T2, an indoor heat exchanger temperature sensor T3, and an indoor temperature sensor T4 are connected to the control unit 16. Further, an irradiation unit 40 is connected to the control unit 16.

The outdoor heat exchanger temperature sensor T1 is installed in the outdoor heat exchanger 8 to detect a temperature of the outdoor heat exchanger 8. The outdoor air temperature sensor T2 is installed in the outdoor unit 3 to detect an outdoor temperature. The indoor heat exchanger temperature sensor T3 is installed in the indoor heat exchanger 4 to detect a temperature of the indoor heat exchanger 4. The indoor temperature sensor T4 is installed in the indoor unit 2 to detect an indoor temperature.

The control unit 16 includes a microcomputer, an input-output circuit, and the like. The control unit 16 controls the operation of the air conditioner 1 by performing operation processing, determination processing, or the like based on a command (such as an operation start command or an indoor temperature setting command) sent from the remote control 17 or various temperatures detected by the outdoor heat exchanger temperature sensor T1, the outdoor air temperature sensor T2, the indoor heat exchanger temperature sensor T3, and the indoor temperature sensor T4.

[Configuration of Indoor Unit]

Figure 3:
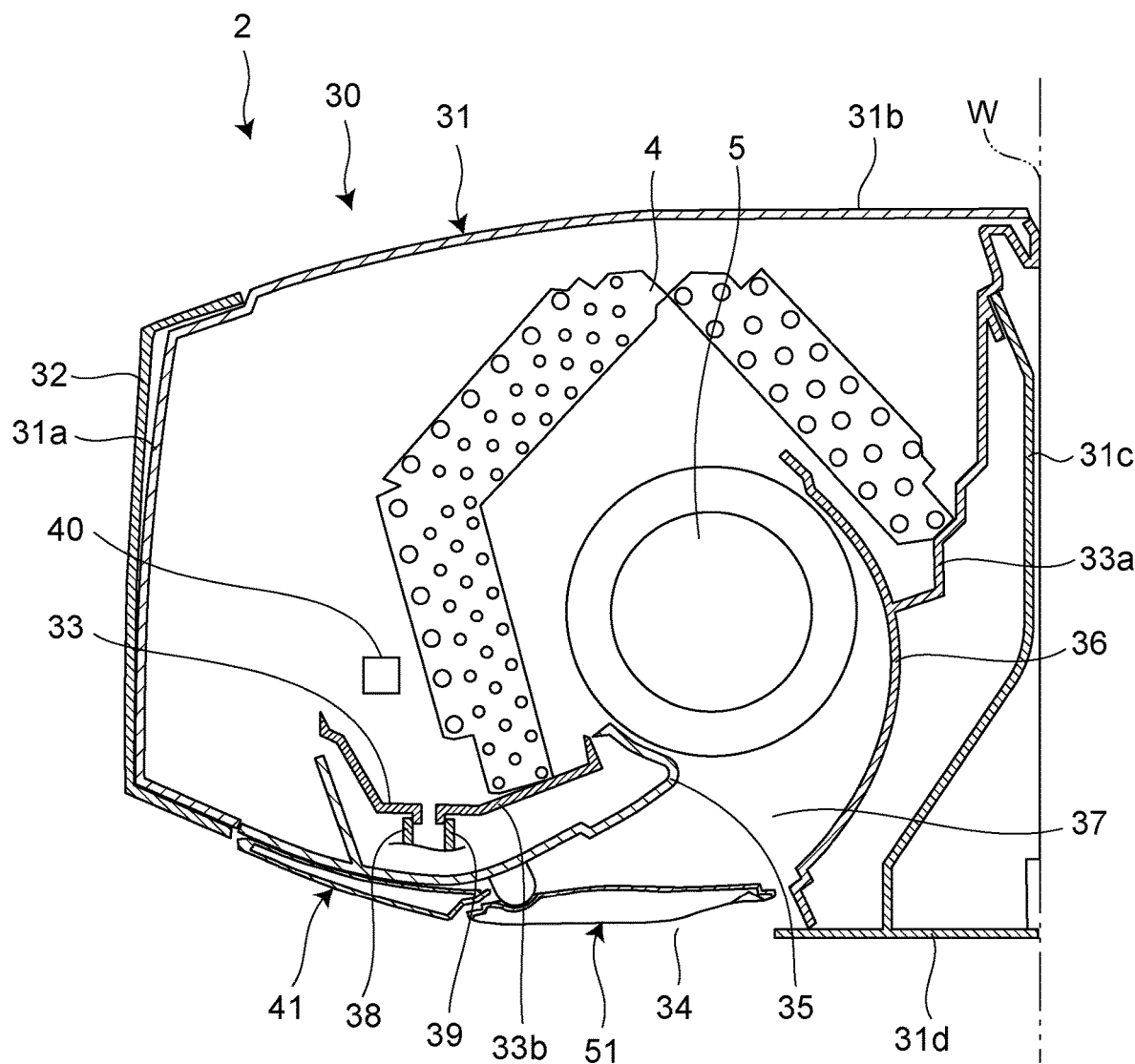
FIG. 3 is a schematic cross-sectional view of an indoor unit that is out of operation, the indoor unit being a component of the air conditioner illustrated in FIG. 1.

FIG. 3 is a schematic cross-sectional view of the indoor unit 2 that is out of operation, the indoor unit 2 being a component of the air conditioner 1. The indoor unit 2 illustrated in FIG. 3 is of a wall-mounted type.

The indoor unit 2 includes a casing 30 including a casing body 31 and a front panel 32. The casing 30 is attached to a wall surface W facing an indoor space and accommodates the indoor fan 5, the indoor heat exchanger 4, the drain pan 33, and the like.

The casing body 31 includes a plurality of members: a front part 31*a*, an upper part 31*b*, a rear part 31*c*, and a lower part 31*d*. The front panel 32 is attached to the front part 31*a* in an openable and closable manner. Further, an intake port (not illustrated) is provided extending from the front part 31*a* to the upper part 31*b*.

The front panel 32 is associated with the front part 31*a* of the indoor unit 2 and has, for example, a flat shape with no intake port. Further, an upper end of the front panel 32 is pivotably supported by the upper part 31*b* of the casing body 31 and thus can swing in a hinged manner.

The indoor fan 5 and the indoor heat exchanger 4 are attached to the casing body 31. The indoor heat exchanger 4 exchanges heat with indoor air drawn into the casing 30 through the intake port. Further, the indoor heat exchanger 4 has an inverted V shape in a side view with both ends extending downward and a bend positioned higher. The indoor heat exchanger 4 includes a plurality of heat transfer tubes and a large number of fins.

The indoor fan 5 is positioned below the bend of the indoor heat exchanger 4. The indoor fan 5 is, for example, a cross-flow fan. The indoor fan 5 forces indoor air passing through the indoor heat exchanger 4 to flow to a blow-out port 34 of the lower part 31*d* of the casing body 31.

The casing body 31 is further provided with a first partition wall 35 and a second partition wall 36. A space between the first partition wall 35 and the second partition wall 36 serves as a blow-out flow path 37 through which the indoor fan 5 and the blow-out port 34 communicate with each other.

The drain pan 33 is disposed below the indoor heat exchanger 4 and receives condensed water generated by condensation on the indoor heat exchanger 4. The drain pan 33 includes an upper receiver 33*a*, a lower receiver 33*b*, and a connecting part (not illustrated) through which the upper receiver 33*a* and the lower receiver 33*b* are connected with each other. The condensed water drops from the indoor heat exchanger 4 into both the upper receiver 33*a* and the lower receiver 33*b*. The condensed water dropped into the upper receiver 33*a* flows down to the lower receiver 33*b* through the connecting portion. The condensed water flowing down from the upper receiver 33*a* to the lower receiver 33*b* and the condensed water dropped into the lower receiver 33*b* accumulate in the lower receiver 33*b* as drain water. The drain water accumulated in the lower receiver 33*b* is drained, by its own weight, outside from a drain port 38 provided in the lower receiver 33*b* through a drain hose 39. That is, the drain pan 33 is structured to cause the drain water to flow out by its own weight.

The control unit 16 controls the cooling operation to make the temperature of the indoor heat exchanger 4 measured by the indoor heat exchanger temperature sensor T3 lower than the dew point, thereby generating drain water. The control unit 16 can estimate a water level of the drain water accumulated in the lower receiver 33*b* of the drain pan 33 based on the operation status of the cooling operation. Therefore, the control unit 16 functions as a detection unit that detects the water level of the drain water accumulated in the drain pan 33. Some air conditioners, e.g., air conditioners installed at high places such as ceiling-embedded air conditioners and ceiling-suspended air conditioners, may have a water level sensor installed as a detection unit that detects the water level of the drain water accumulated in the drain pan 33.

The irradiation unit 40 (illustrated in FIG. 2 but not illustrated in FIG. 3) is provided above the drain pan 33. The irradiation unit 40 emits deep ultraviolet rays (hereinafter, referred to as "ultraviolet rays") having a relatively short wavelength among ultraviolet rays to irradiate an upper surface of the drain pan 33 with the ultraviolet rays. The irradiation unit 40 is, for example, an ultraviolet LED (light emitting diode). The ultraviolet rays emitted by the irradiation unit 40 have a wavelength of, for example, 255 nm to 350 nm.

In order to denature or inactivate bacteria, mold, or the like contained in the drain water i.e., to perform sterilization, it is necessary to emit the ultraviolet rays by a predetermined dose. The dose of the ultraviolet rays to be emitted is determined by multiplying the ultraviolet intensity by the irradiation time, that is, by the ultraviolet intensity*the irradiation time. In order to achieve a certain predetermined dose, when the irradiation unit 40 is turned on at half the rating in accordance with a pattern B, the ultraviolet intensity becomes half the ultraviolet intensity when the irradiation unit 40 is turned on at the rating in accordance with a pattern A, and the irradiation time becomes twice the irradiation time when the irradiation unit 40 is turned on in accordance with the pattern A. Making the dose during the cooling operation and the dose after the cooling operation equal to each other makes their respective sterilization degrees equal to each other. The control unit 16 controls the ultraviolet intensity and the irradiation time of the irradiation unit 40.

The irradiation unit 40 irradiates the drain pan 33 with the ultraviolet rays by the predetermined dose to sterilize the drain water accumulated in the drain pan 33, so that propagation of bacteria, mold, or the like in the drain water accumulated in the drain pan 33 is suppressed.

The indoor unit 2 includes a first horizontal flap 41 and a second horizontal flap 51 disposed behind the first horizontal flap 41 (adjacent to the wall surface W). The first horizontal flap 41 and the second horizontal flap 51 adjust a vertical direction of air blowing out from the blow-out port 34 (air flowing through the blow-out flow path 37). The first horizontal flap 41 is pivotably attached to the lower part 31d of the casing body 31. In the state illustrated in FIG. 3, the indoor fan 5 is stopped, the front panel 32, the first horizontal flap 41, and the second horizontal flap 51 are closed, and the air conditioning operation by the indoor unit 2 is stopped. Note that the first horizontal flap 41 is an example of a first horizontal blade. Further, the second horizontal flap 51 is an example of a second horizontal blade.

The indoor unit 2 further includes a plurality of vertical flaps (not illustrated) that adjust a lateral direction of air blowing out. The plurality of vertical flaps are arranged in the blow-out flow path 37 at predetermined intervals in a longitudinal direction of the blow-out port 34 (a direction perpendicular to the drawing sheet of FIG. 3). Note that the vertical flap is an example of a perpendicular blade.

[Control of Irradiation with Ultraviolet Rays]

Figure 4:
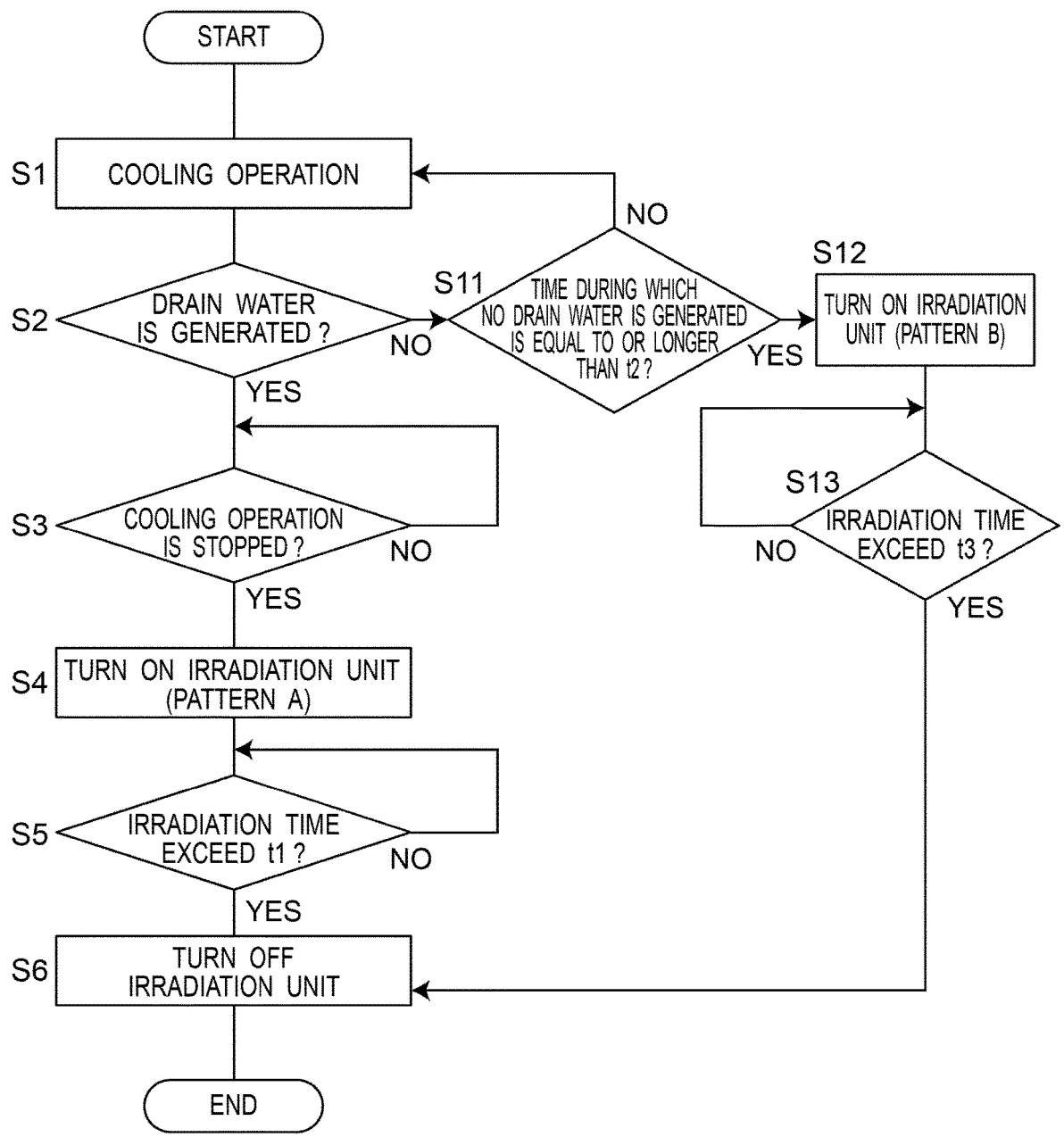
FIG. 4 is a control flowchart of irradiation with ultraviolet rays performed by the air conditioner.

Next, control of irradiation with ultraviolet rays performed by the air conditioner 1 will be described with reference to FIG. 4. FIG. 4 is a control flowchart of irradiation with ultraviolet rays performed by the air conditioner 1.

In the air conditioner 1, when the cooling operation is selected by operation of the remote control 17 made by the user, the control unit 16 performs the cooling operation desired by the user to place the air conditioner 1 in the cooling operation over a predetermined period of time (step S1).

In step S2, the control unit 16 determines whether drain water has been generated. Specifically, drain water is generated during the normal cooling operation (YES in step S2), and the process proceeds to step S3 accordingly.

In step S3, the control unit 16 determines whether the cooling operation is stopped. When the cooling operation is not stopped (NO in step S3), the process waits until the cooling operation is stopped. When the cooling operation is stopped (YES in step S3), the process proceeds to step S4.

In step S4, the control unit 16 controls the irradiation unit 40 to turn on the irradiation unit 40. Specifically, the control unit 16 applies, in accordance with the pattern A, a rated current and a rated voltage to the irradiation unit 40 to control the irradiation unit 40 so as to cause the irradiation unit 40 to perform irradiation with rated total radiant flux. Accordingly, the drain water accumulated in the drain pan 33 is irradiated with ultraviolet rays.

In step S5, the control unit 16 determines whether the irradiation time of the irradiation unit 40 exceeds a predetermined first time t1 necessary for sterilization. The predetermined first time t1 is, for example, 1 hour, but varies in a manner that depends on the intensity of the ultraviolet rays from the irradiation unit 40. When the irradiation time is less than the predetermined first time t1 (NO in step S5), the process waits until the predetermined first time t1 elapses. This causes the drain water accumulated in the drain pan 33 to be sterilized, and propagation of bacteria, mold, or the like in the drain water accumulated in the drain pan 33 is suppressed accordingly. When the irradiation time exceeds the predetermined first time t1 (YES in step S5), the process proceeds to step S6.

When no drain water is generated in step S2 (NO in step S2), the process proceeds to step S11.

In step S11, the control unit 16 determines whether a time during which no drain water is generated accumulated from the start of the cooling operation is equal to or longer than a predetermined second time t2. Even during the cooling operation, when an accumulated time during which the water level of the drain water is equal to or lower than a predetermined level becomes longer than the predetermined second time t2, bacteria, mold, or the like easily propagates. That is, when the humidity of the indoor space decreases due to long cooling operation, and as a result, the state where the drain water is low in water level continues for a predetermined time (second time t2), old drain water is not replaced with new drain water, so that bacteria, mold, or the like easily propagates. The predetermined second time t2 is in a range of, for example, 10 hours to 12 hours, but varies in a manner that depends on propagation conditions of bacteria, mold, or the like. When the accumulated time during which no drain water is generated is shorter than the predetermined second time t2 (NO in step S11), the cooling operation continues. When the accumulated time during which no drain water is generated is equal to or longer than the predetermined second time t2 (YES in step S11), the process proceeds to step S12.

In step S12, the control unit 16 controls the irradiation unit 40 to cause the irradiation unit 40 to perform, in accordance with the pattern B, irradiation with total radiant flux less than the rated total radiant flux during the cooling operation. Accordingly, the drain water accumulated in the drain pan 33 is irradiated with ultraviolet rays. For example, the control unit 16 controls the irradiation unit 40 to cause the irradiation unit 40 to perform, in accordance with the pattern B, irradiation with 50% of the rated total radiant flux. This makes the ultraviolet intensity after the cooling operation (pattern A) larger than the ultraviolet intensity during the cooling operation (pattern B).

In step S13, the control unit 16 determines whether the irradiation time of the irradiation unit 40 exceeds a predetermined third time t3 necessary for sterilization. When the irradiation time is less than the predetermined third time t3 (NO in step S13), the process waits until the predetermined third time t3 elapses. The dose of the ultraviolet rays necessary for sterilization is determined by the ultraviolet intensity*the irradiation time. Since the ultraviolet intensity during the cooling operation (pattern B) is smaller than the ultraviolet intensity after the cooling operation (pattern A), the irradiation time (third time t3) during the cooling operation (pattern B) is longer than the irradiation time (first time t1) after the cooling operation (pattern A). For example, when the irradiation unit 40 is controlled in accordance with the pattern B to perform irradiation with 50% of the rated total radiant flux, the irradiation time (third time t3) during the cooling operation (pattern B) becomes twice the irradiation time (first time t1) after the cooling operation (pattern A). Making the irradiation time during the cooling operation (pattern B) longer causes the drain water accumulated in the drain pan 33 to be sterilized, and propagation of bacteria, mold, or the like in the drain water accumulated in the drain pan 33 is suppressed accordingly. When the irradiation time exceeds the predetermined third time t3 (YES in step S13), the process proceeds to step S6.

In step S6, the control unit 16 controls the irradiation unit 40 to turn off the irradiation unit 40. When the irradiation unit 40 is turned off, the control of the irradiation with ultraviolet rays is brought to an end.

In the air conditioner 1, the irradiation unit 40 is controlled to make the ultraviolet intensity after the cooling operation larger than the ultraviolet intensity during the cooling operation, in other words, to make the ultraviolet intensity during the cooling operation smaller than the ultraviolet intensity after the cooling operation. This makes it possible to effectively perform sterilization after the cooling operation that requires large ultraviolet intensity and make the life of the irradiation unit 40 longer thanks to lower ultraviolet intensity during the cooling operation.

Other Embodiment

Figure 5:
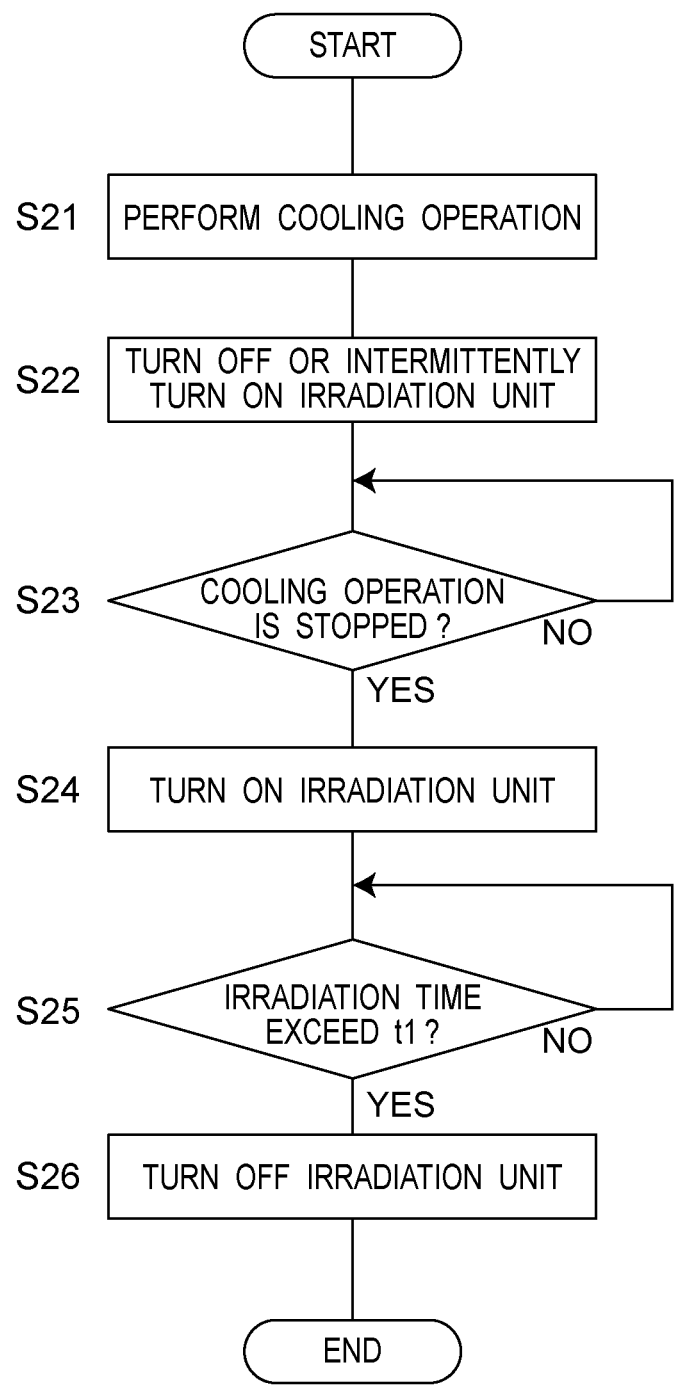
FIG. 5 is a control flowchart of irradiation with ultraviolet rays performed by the air conditioner according to the other embodiment.

Next, control of irradiation with ultraviolet rays performed by the air conditioner 1 according to the other embodiment will be described with reference to FIG. 5. FIG. 5 is a control flowchart of the irradiation with ultraviolet rays performed by the air conditioner 1 according to the other embodiment.

In the air conditioner 1, when the cooling operation is selected by operation of the remote control 17 made by the user, the control unit 16 performs the cooling operation desired by the user to place the air conditioner 1 in the cooling operation over a predetermined period of time (step S21).

In step S22, the control unit 16 controls the irradiation unit 40 to bring the irradiation unit 40 into a turn-off state or intermittently turn on the irradiation unit 40 during the cooling operation. Specifically, the turn-off state is to keep the ultraviolet intensity of the irradiation unit 40 at zero from the start of the cooling operation, and the intermittent turn-on is to repeat turning on and off at least once at a predetermined timing during the cooling operation.

In step S23, the control unit 16 determines whether the cooling operation is stopped. When the cooling operation is not stopped (NO in step S23), the process waits until the cooling operation is stopped. When the cooling operation is stopped (YES in step S23), the process proceeds to step S24.

In step S24, the control unit 16 controls the irradiation unit 40 to turn on the irradiation unit 40. Specifically, the control unit 16 applies, in accordance with the pattern A, a rated current and a rated voltage to the irradiation unit 40 to control the irradiation unit 40 so as to cause the irradiation unit 40 to perform irradiation with rated total radiant flux. Accordingly, the drain water accumulated in the drain pan 33 is irradiated with ultraviolet rays.

In step S25, the control unit 16 determines whether the irradiation time of the irradiation unit 40 exceeds the predetermined first time t1 necessary for sterilization. When the irradiation time is less than the predetermined first time t1 (NO in step S25), the process waits until the predetermined first time t1 elapses. This causes the drain water accumulated in the drain pan 33 to be sterilized, and propagation of bacteria, mold, or the like in the drain water accumulated in the drain pan 33 is suppressed accordingly. When the irradiation time exceeds the predetermined first time t1 (YES in step S25), the process proceeds to step S26.

In step S26, the control unit 16 controls the irradiation unit 40 to turn off the irradiation unit 40. When the irradiation unit 40 is turned off, the control of the irradiation with ultraviolet rays is brought to an end.

The air conditioner 1 makes the irradiation time of the ultraviolet rays during the cooling operation shorter, so that it is possible to make the life of the irradiation unit 40 longer by a time during which the irradiation with the ultraviolet rays is not performed during the cooling operation.

The embodiments of the present disclosure have been described above. However, it should be understood that specific configurations of the present disclosure are not limited to those described in the embodiments. The scope of the present disclosure is defined by not only the embodiments described above but also the appended claims and further includes equivalents of the claims and all modifications within the scope of the claims.

When irradiation with ultraviolet rays is performed in a state where no drain water accumulates in the drain pan 33, the irradiation with ultraviolet rays has no effect. Therefore, in the air conditioner 1, the irradiation unit 40 is controlled to irradiate drain water accumulated in the drain pan 33 with ultraviolet rays. This makes the irradiation time of the irradiation unit 40 short as compared with a case where the irradiation with ultraviolet rays continues without stop during the cooling operation, so that it is possible to effectively sterilize the drain water.

The air conditioner 1 according to the one embodiment and the other embodiment includes a detection unit 16 that detects the water level of the drain water. The control unit 16 can control the irradiation unit 40 to irradiate the drain pan 33 with the ultraviolet rays when an accumulated time during which the water level of the drain water detected by the detection unit 16 is equal to or lower than a predetermined level becomes equal to or longer than a predetermined time during the cooling operation.

Even during the cooling operation, when an accumulated time during which the water level of the drain water is equal to or lower than the predetermined level becomes equal to or longer than the predetermined time, bacteria, mold, or the like easily propagates due to the drain water remaining on the drain pan 33 for a long time. In the air conditioner configured as described above, the drain water is irradiated with the ultraviolet rays, so that propagation of bacteria, mold, or the like in the drain water is suppressed.

The air conditioner 1 according to the one embodiment and the other embodiment includes the indoor heat exchanger temperature sensor T3 that detects a temperature of the indoor heat exchanger 4. The control unit 16 controls the irradiation unit 40 to irradiate the drain pan 33 with the ultraviolet rays when an accumulated time during which the temperature of the indoor heat exchanger 4 detected by the indoor heat exchanger temperature sensor T3 is equal to or higher than a dew-point temperature becomes equal to or longer than the predetermined time t2 during the cooling operation.

The dew-point temperature is calculated based on, for example, an indoor temperature detected by the indoor temperature sensor T4, an amount of indoor moisture (for example, relative humidity) detected by a humidity sensor T5, and a dew-point temperature calculation table stored in a storage unit of the control unit 16.

Even during the cooling operation, when an accumulated time during which the temperature of the indoor heat exchanger 4 is equal to or higher than the dew-point temperature becomes equal to or longer than the predetermined time t2, bacteria, mold, or the like easily propagates due to the drain water remaining on the drain pan 33 for a long time. In the air conditioner 1 configured as described above, the drain water is irradiated with the ultraviolet rays, so that propagation of bacteria, mold, or the like in the drain water is suppressed.

The air conditioner 1 according to the one embodiment and the other embodiment includes the indoor temperature sensor T4 that detects an indoor temperature. The control unit 16 controls the irradiation unit 40 to emit the ultraviolet rays when a temperature difference between the indoor temperature detected by the indoor temperature sensor T4 and a set temperature becomes equal to or less than a predetermined temperature during the cooling operation.

During the cooling operation, the indoor temperature approaches the set temperature and is stably maintained, which eliminates the need of cooling the indoor heat exchanger 4. Therefore, even during the cooling operation, when the temperature difference between the indoor temperature and the set temperature is equal to or less than the predetermined temperature, cooling of the indoor heat exchanger 4 is stopped, so that the generation of drain water is suppressed. Therefore, the air conditioner 1 configured as described above makes the irradiation time of the ultraviolet rays during the cooling operation shorter, so that it is possible to make the life of the irradiation unit 40 longer. Note that the set temperature is set by the user or set by the control unit 16. When the temperature difference between the indoor temperature and the set temperature becomes equal to or less than the predetermined temperature, the irradiation with ultraviolet rays is continuously or intermittently performed. The continuous irradiation with ultraviolet rays when the temperature difference is equal to or less than the predetermined temperature serves as the intermittent irradiation with ultraviolet rays during the cooling operation.

REFERENCE SIGNS LIST 1 air conditioner
2 indoor unit
3 outdoor unit
4 indoor heat exchanger (heat exchanger)
6 compressor
7 four-way switching valve
8 outdoor heat exchanger (heat exchanger)
10 expansion valve
11 accumulator
14 indoor-unit controller (control unit)
15 outdoor-unit controller (control unit)
16 control unit
17 remote controller (remote control)
30 casing
31 casing body
31a front part
31b upper part
31c rear part
31d lower part
32 front panel
33 drain pan
34 blow-out port
35 first partition wall
36 second partition wall
37 blow-out flow path
38 drain port
39 drain hose
40 irradiation unit
41 first horizontal flap
51 second horizontal flap
L1, L2 connection pipe
T1 outdoor heat exchanger temperature sensor
T2 outdoor air temperature sensor
T3 indoor heat exchanger temperature sensor (temperature sensor)
T4 indoor temperature sensor
T5 humidity sensor
W wall surface

What is claimed is:

1. An air conditioner comprising:
a heat exchanger provided in an indoor unit of the air conditioner;
a drain pan configured to receive drain water generated in the heat exchanger;
an irradiation unit configured to irradiate the drain pan with ultraviolet rays;
a controller configured to control ultraviolet intensity of the ultraviolet rays from the irradiation unit; and
a water sensor configured to detect a water level of the drain water,
wherein
the controller controls the irradiation unit to make the ultraviolet intensity after a cooling operation larger than the ultraviolet intensity during the cooling operation,
the irradiation unit comprises a light emitter, and
the controller controls the irradiation unit to irradiate the drain pan with the ultraviolet rays when an accumulated time during which the water level of the drain water detected by the water sensor is equal to or lower than a predetermined level becomes equal to or longer than a predetermined time during the cooling operation.

2. An air conditioner comprising:
a heat exchanger provided in an indoor unit of the air conditioner;
a drain pan configured to receive drain water generated in the heat exchanger;
an irradiation unit configured to irradiate the drain pan with ultraviolet rays;
a controller configured to control ultraviolet intensity of the ultraviolet rays from the irradiation unit; and
a temperature sensor configured to detect a temperature of the heat exchanger,
wherein
the controller controls the irradiation unit to make the ultraviolet intensity after a cooling operation larger than the ultraviolet intensity during the cooling operation,
the irradiation unit comprises a light emitter, and
the controller controls the irradiation unit to irradiate the drain pan with the ultraviolet rays when an accumulated time during which the temperature of the heat exchanger detected by the temperature sensor is equal to or higher than a dew-point temperature becomes equal to or longer than a predetermined time during the cooling operation.

3. An air conditioner comprising:
a heat exchanger provided in an indoor unit of the air conditioner;
a drain pan configured to receive drain water generated in the heat exchanger;
an irradiation unit configured to irradiate the drain pan with ultraviolet rays;
a controller configured to control ultraviolet intensity of the ultraviolet rays from the irradiation unit; and
an indoor temperature sensor configured to detect an indoor temperature,
wherein
the controller controls the irradiation unit to make the ultraviolet intensity after a cooling operation larger than the ultraviolet intensity during the cooling operation,
the irradiation unit comprises a light emitter,
the controller controls the irradiation unit to emit the ultraviolet rays when a temperature difference between the indoor temperature detected by the indoor temperature sensor and a set temperature selected by a user or the controller becomes equal to or less than a predetermined temperature during the cooling operation, and
the controller controls the irradiation unit to make a dose obtained by multiplying the ultraviolet intensity by the irradiation time during the cooling operation equal to a dose obtained by multiplying the ultraviolet intensity by the irradiation time after the cooling operation.

4. An air conditioner comprising:
a heat exchanger provided in an indoor unit of the air conditioner;
a drain pan configured to receive drain water generated in the heat exchanger;
an irradiation unit configured to irradiate the drain pan with ultraviolet rays; and
a controller configured to control ultraviolet intensity of the ultraviolet rays from the irradiation unit,
wherein
the controller controls the irradiation unit to make the ultraviolet intensity after a cooling operation larger than the ultraviolet intensity during the cooling operation,
the irradiation unit comprises a light emitter,
the controller controls an irradiation time of the irradiation unit, and
the controller controls the irradiation unit to make the irradiation time during the cooling operation longer than the irradiation time after the cooling operation.

5. The air conditioner according to claim 1, wherein the controller controls the irradiation unit to make a dose obtained by multiplying the ultraviolet intensity by the irradiation time during the cooling operation equal to a dose obtained by multiplying the ultraviolet intensity by the irradiation time after the cooling operation.

6. The air conditioner according to claim 1, wherein the drain pan is structured to cause the drain water to flow out by its own weight.

7. An air conditioner comprising:
a heat exchanger provided in an indoor unit of the air conditioner;
a drain pan configured to receive drain water generated in the heat exchanger;
an irradiation unit configured to irradiate the drain pan with ultraviolet rays;
a controller configured to control the irradiation unit; and
a water sensor configured to detect a water level of the drain water,
wherein
the controller controls the irradiation unit to emit the ultraviolet rays intermittently or to emit no ultraviolet rays during a cooling operation,
the irradiation unit comprises a light emitter, and
the controller controls the irradiation unit to irradiate the drain pan with the ultraviolet rays when an accumulated time during which the water level of the drain water detected by the water sensor is equal to or lower than a predetermined level becomes equal to or longer than a predetermined time during the cooling operation.

8. An air conditioner comprising:
a heat exchanger provided in an indoor unit of the air conditioner;
a drain pan configured to receive drain water generated in the heat exchanger;
an irradiation unit configured to irradiate the drain pan with ultraviolet rays;
a controller configured to control the irradiation unit; and
a temperature sensor configured to detect a temperature of the heat exchanger,
wherein
the controller controls the irradiation unit to emit the ultraviolet rays intermittently or to emit no ultraviolet rays during a cooling operation,
the irradiation unit comprises a light emitter, and
the controller controls the irradiation unit to irradiate the drain pan with the ultraviolet rays when an accumulated time during which the temperature of the heat exchanger detected by the temperature sensor is equal to or higher than a dew-point temperature becomes equal to or longer than a predetermined time during the cooling operation.

9. The air conditioner according to claim 7, wherein the drain pan is structured to cause the drain water to flow out by its own weight.

10. The air conditioner according to claim 8, wherein the drain pan is structured to cause the drain water to flow out by its own weight.

11. The air conditioner according to claim 2, wherein the controller controls the irradiation unit to make a dose obtained by multiplying the ultraviolet intensity by the irradiation time during the cooling operation equal to a dose obtained by multiplying the ultraviolet intensity by the irradiation time after the cooling operation.

12. The air conditioner according to claim 4, wherein the controller controls the irradiation unit to make a dose obtained by multiplying the ultraviolet intensity by the irradiation time during the cooling operation equal to a dose obtained by multiplying the ultraviolet intensity by the irradiation time after the cooling operation.

13. The air conditioner according to claim 2, wherein the drain pan is structured to cause the drain water to flow out by its own weight.

14. The air conditioner according to claim 3, wherein the drain pan is structured to cause the drain water to flow out by its own weight.

15. The air conditioner according to claim 4, wherein the drain pan is structured to cause the drain water to flow out by its own weight.

* * * * *